(12) United States Patent
Murai et al.

(10) Patent No.: US 7,661,577 B2
(45) Date of Patent: Feb. 16, 2010

(54) IMIDAZOLE COMPOUND AND USE THEREOF

(75) Inventors: Takayuki Murai, Kagawa (JP);
Yoshimasa Kikukawa, Kagawa (JP);
Hirohiko Hirao, Kagawa (JP)

(73) Assignee: Shikoku Chemicals Corporation, Marugame-Shi (JP)

(*) Notice: Subject to any disclaimer, the term of this patent is extended or adjusted under 35 U.S.C. 154(b) by 112 days.

(21) Appl. No.: 10/548,544

(22) PCT Filed: Mar. 18, 2004

(86) PCT No.: PCT/JP2004/003658

§ 371 (c)(1),
(2), (4) Date: Sep. 13, 2005

(87) PCT Pub. No.: WO2004/083487

PCT Pub. Date: Sep. 30, 2004

(65) Prior Publication Data

US 2007/0113930 A1 May 24, 2007

(30) Foreign Application Priority Data

Mar. 19, 2003 (JP) ............... 2003-075030
Sep. 29, 2003 (JP) ............... 2003-338527
Jan. 29, 2004 (JP) ............... 2004-022241
Feb. 4, 2004 (JP) ............... 2004-028613

(51) Int. Cl.
*B23K 1/20* (2006.01)

(52) U.S. Cl. ..................... 228/214; 148/269

(58) Field of Classification Search ............. 228/214; 148/269, 273
See application file for complete search history.

(56) References Cited

U.S. PATENT DOCUMENTS 5,498,301 A * 3/1996 Hirao et al. ............... 148/269
6,264,093 B1 * 7/2001 Pilukaitis et al. ......... 228/180.1

FOREIGN PATENT DOCUMENTS

EP 0627499 A1 12/1994
JP 2002-105662 4/2002

OTHER PUBLICATIONS

European Search Report dated Nov. 17, 2006.
European Search Report dated Sep. 23, 2006.
* cited by examiner

*Primary Examiner*—Jessica L. Ward
*Assistant Examiner*—Nicholas P D'Aniello
(74) *Attorney, Agent, or Firm*—Kratz, Quintos & Hanson, LLP

(57) ABSTRACT

A water-based composition for treating copper or copper alloy surface for lead-free soldering, the composition comprising a compound represented by general formula (1):

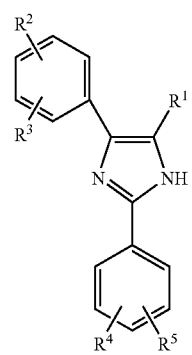

(1)

wherein $R^1$ is hydrogen or methyl, and either $R^2$ and $R^3$ represent chlorine and $R^4$ and $R^5$ represent hydrogen, or $R^2$ and $R^3$ represent hydrogen and $R^4$ and $R^5$ represent chlorine.

1 Claim, No Drawings

IMIDAZOLE COMPOUND AND USE THEREOF

TECHNICAL FIELD

The present invention relates to a novel imidazole compound, a copper or copper alloy surface treatment agent and composition for lead-free soldering, a method for treating copper or copper alloy surfaces, and a method for soldering copper or copper alloys.

BACKGROUND OF THE INVENTION

In recent years, surface mount technology with high density has been widely adopted. Such surface mount technologies are classified, among others, into double-sided surface mount technology in which chip type parts are joined with use of solder paste, and hybrid mount technology which is a combination of surface mount technology of chip type parts using solder paste and through-hole mount technology of discrete parts. In either mount process, a printed wiring board is subjected to two or more soldering steps, and thus it is exposed to high temperatures resulting in a severe thermal history.

Oxide film formation is accelerated by heating the surface of copper or copper alloys constituting the circuit part of a printed wiring board, and thus the surface of the circuit part cannot maintain good solderability.

In order to protect the copper circuit part of the printed wiring board from air oxidation, a chemical layer is generally formed on the surface of the circuit part using a surface treating agent. It is necessary, however, that good solderability be maintained by preventing the chemical layer from degenerating (i.e., being degraded) to protect the copper circuit part even after the copper circuit part has a thermal history of multiple cycles.

Tin-lead alloy eutectic solders have been conventionally used for mounting electronic components to a printed wiring board, etc. In recent years, however, concerns have developed that the lead contained in the solder alloy adversely affects the human body, and thus the use of lead-free solder is desired.

Accordingly, various lead-free solders are being considered. For example, lead-free solders have been suggested in which one or more metals, such as silver, zinc, bismuth, indium, antimony, copper, etc., are added to a base metal of tin.

The conventionally used tin-lead eutectic solder is excellent in wettability on the surface of substrate, particularly copper, and thus strongly adheres to copper, resulting in high reliability. In contrast, lead-free solder is inferior to the conventionally used tin-lead solder in wettability on a copper surface, and thus exhibits poor solderability and low bonding strength due to voids and other bonding defects.

Therefore, when using lead-free solder, it is necessary to select a solder alloy with superior solderability and a flux which is suitable for use with lead-free solder. A surface treatment agent for use in preventing oxidation on the surface of copper or a copper alloy is also required to have functions for improving the wettability and solderability of the lead-free solder.

Many lead-free solders have a high melting point, and a soldering temperature that is about 20 to about 50° C. higher than that of the conventionally used tin-lead eutectic solder. Thus, the surface treatment agent for use in the process of soldering with lead-free solder should have the characteristic of being able to form a chemical layer with excellent heat resistance.

Many imidazole compounds, such as 2-alkylimidazole, 2-arylimidazole, 2-alkylbenzimidazole, 2-arylbenzimidazole, 2-aralkylbenzimidazole compounds, etc., have been considered as active ingredients for a surface treatment agent. All of these imidazole compounds, however, have been considered for use with a tin-lead eutectic solder, and thus give insufficient wettability, resulting in inadequate solderability when used for use in the process of soldering with lead-free solder.

U.S. Pat. Nos. 5,498,301 and 5,560,785 and EP 0627499 A1, for example, propose a surface treatment agent containing as an active ingredient an imidazole compound having an aryl group at the 2- and 4-positions of an imidazole ring and represented by general formula (A),

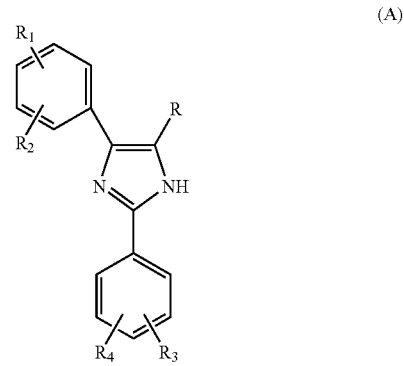

(A)

wherein R is hydrogen or methyl; $R_1$ and $R_2$ are hydrogen, lower alkyl or halogen; and $R_3$ and $R_4$ are hydrogen, lower alkyl, halogen, lower alkoxy, di-lower alkylamino, cyano or nitro. These references disclose in Example 10 a surface treatment agent containing 2-(2,4-dichlorophenyl)-4-phenyl-5-methylimidazole as an active ingredient, and disclose that tests for solder wettability and spreadability of a solder paste were carried out using said surface treatment agent.

However, the solder used in these tests was a tin-lead eutectic solder, and the references are totally silent as to whether solder wettability is improved and good solderability is attained when lead-free solder is used.

Japanese Unexamined Patent Publication No. 7-243053 discloses 2,4-diphenylimidazole and 2,4-diphenyl-5-methylimidazole as a surface treatment agent for copper and copper alloys. It is also disclosed in Examples thereof that 2,4-diphenylimidazole and 2,4-diphenyl-5-methylimidazole are used as a surface treatment agent for copper and copper alloys, particularly for improving the solder wettability and solder flow-up rate of a solder paste containing lead.

This publication also discloses a process for synthesizing 2,4-diphenylimidazole as illustrated by the following reaction scheme (1):

Reaction Scheme (1)

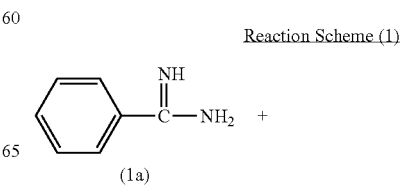

(1a)

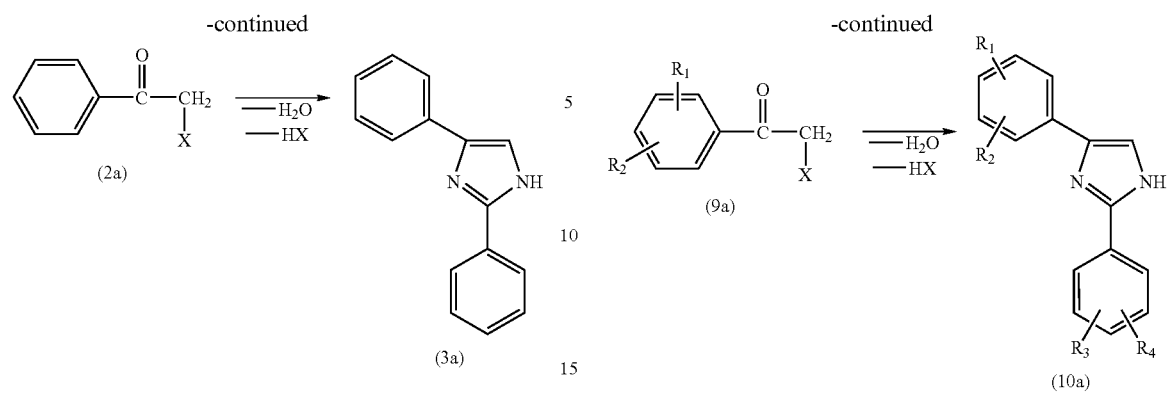

wherein X is chlorine or bromine, and additionally a process for synthesizing 2,4-diphenyl-5-methylimidazole as illustrated by the following reaction scheme (2):

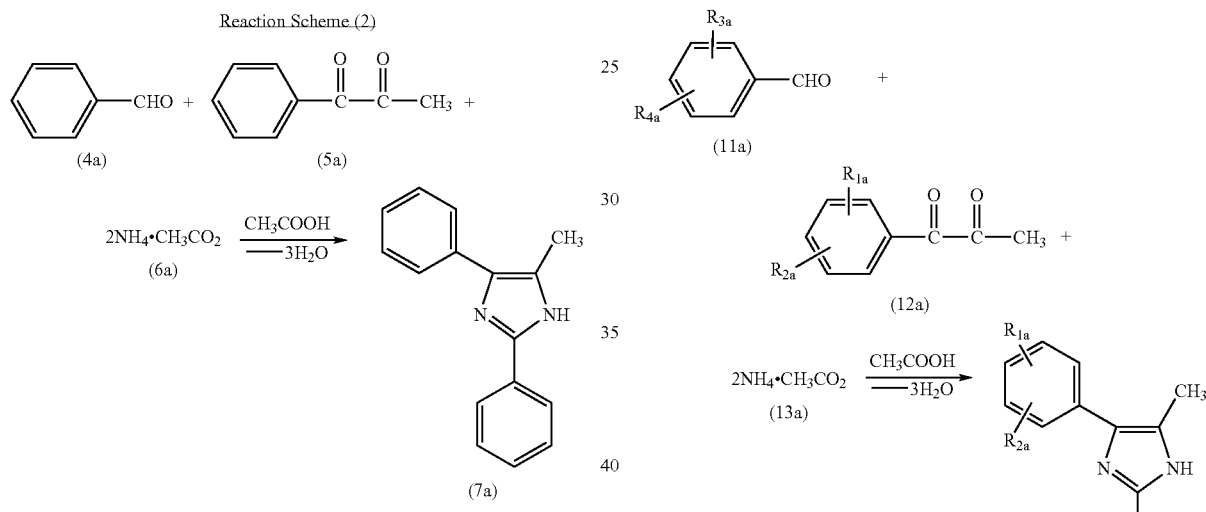

U.S. Pat. No. 5,498,301 (p. 4) and EP 0627499 A1 (p. 5) corresponding to Japanese Unexamined Patent Publication No. 7-243053 suggest that 2-phenyl-4-(dichlorophenyl)imidazole and 2-phenyl-4-(dichlorophenyl)-5-methylimidazole in which hydrogen atoms of phenyl at the 4-position are substituted with two chlorine atoms are useful as a surface treatment agent for copper, in particular as a treatment agent for improving the solder wettability and solder flow-up rate of a solder paste containing lead. Further, these references suggest a process for producing an imidazole compound having one or more substituents at each phenyl group of the 2- and 4-positions by the following reaction schemes (3) and (4).

Reaction Scheme (3)

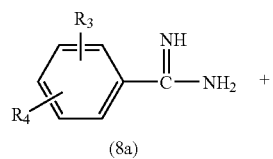

wherein $R_1$ and $R_2$ are hydrogen, lower alkyl or halogen; and $R_3$ and $R_4$ are hydrogen, lower alkyl, halogen, lower alkoxy, di-lower alkylamino or nitro.

wherein $R_{1a}$ and $R_{2a}$ are hydrogen, lower alkyl or halogen; and $R_{3a}$ and $R_{4a}$ are hydrogen, lower alkyl, halogen, lower alkoxy, di-lower alkylamino or nitro.

Neither U.S. Pat. No. 5,498,301 nor EP 0627499 A1, however, disclose that 2-phenyl-4-(dichlorophenyl)imidazole and 2-phenyl-4-(dichlorophenyl)-5-methylimidazole were actually synthesized. No CAS Registry Number is given to these compounds either.

Especially, the reaction scheme (4) seemingly suggests that 2-phenyl-4-(dichlorophenyl)-5-methylimidazole compounds having a methyl group at the 5-position can be synthesized from benzaldehyde, 1-(dichlorophenyl)-1,2-propanedione compound and ammonium acetate. Actually, however, while benzaldehyde and ammonium acetate are readily available as industrial chemicals, said 1-(dichlorophenyl)-1,2-propanedione compound is not commercially available as an industrial chemical or as a reagent, and thus cannot be obtained unless synthesized, A process for synthesizing 1-phenyl-1,2-propanedione compounds is disclosed in U.S. Pat. No. 4,107,210. The inventors attempted to synthesize 1-(2,4-dichlorophenyl)-1, 2-propanedione and 1-(3,4-dichlorophenyl)-1,2-propanedione according to the disclosed process. However, the desired products could not be isolated since the reaction was complicated and an appropriate purification method could not be found in either case. Thus, 2-phenyl-4-(dichlorophenyl)-5-methylimidazole compounds have not yet been successfully synthesized based on the reaction scheme (4).

The above-described U.S. Pat. No. 5,498,301 (the left column, line 27, page 4, and Example 10 in the right column, page 7), U.S. Pat. No. 5,560,785 (left column, line 24, page 4, and Example 10 in the left column, page 7) and EP 0627499 A1 (first line, page 6, and Example 10 on page 10) disclose using 2-(2,4-dichlorophenyl)-4-phenyl-5-methylimidazole as a surface treatment agent for copper.

However, other imidazole compounds in which phenyl at the 2-position is substituted with two chlorine atoms are not known.

DISCLOSURE OF THE INVENTION

A first object of the present invention is to provide a novel imidazole compound useful as an agent for treating copper and copper alloy surfaces.

A second object of the invention is to provide a composition for treating copper or copper alloy surfaces which gives excellent solderability between lead-free solder and the surface of the copper or copper alloy constituting a circuit part, etc., of a printed wiring board, when electronic components, etc., are joined to the printed wiring board using lead-free solder.

A third object of the present invention is to provide a process for treating copper or copper alloy surface which gives good solderability between lead-free solder and the surface of the copper or copper alloy constituting a circuit part, etc., of a printed wiring board, when electronic components etc., are joined to a printed wiring board using lead-free solder.

A fourth object of this invention is to provide a soldering process which gives good solderability to copper or copper alloy surfaces when lead-free solder is used.

The inventors carried out intensive research to achieve the above-mentioned objects and obtained the following findings.

(i) An imidazole compound represented by general formula (1):

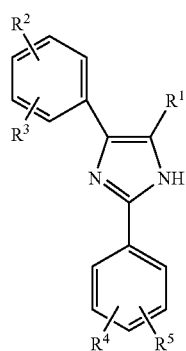

wherein $R^1$ is hydrogen or methyl, and either $R^2$ and $R^3$ represent chlorine and $R^4$ and $R^5$ represent hydrogen, or $R^2$ and $R^3$ represent hydrogen and $R^4$ and $R^5$ represent chlorine, is useful as a component of a water-based composition for a surface treatment of copper or copper alloys, in particular, as a component of a water-based surface treatment composition for use in the formation of a chemical layer when performing lead-free soldering.

(ii) Specifically, a chemical layer with excellent heat-resistance, that is, capable of withstanding a high soldering temperature during lead-free soldering, can be formed on the surface of a copper circuit part by treating a printed wiring board provided with a copper circuit part with a surface treatment composition containing such a compound.

(iii) When the surface treatment composition containing such a compound is used for treating a printed wiring board provided with a copper circuit part, wettability of lead-free solder on copper or copper alloy surfaces can be improved at the time of soldering using lead-free solder, and as a result good solderability, in particular good solder flow-up rate and spreadability of the solder, can be attained.

The present invention has been accomplished based on the above-described findings and provides the following imidazole compounds and others.

Item 1. A water-based composition for treating copper or copper alloy surfaces for lead-free soldering, the composition comprising an imidazole compound represented by general formula (1):

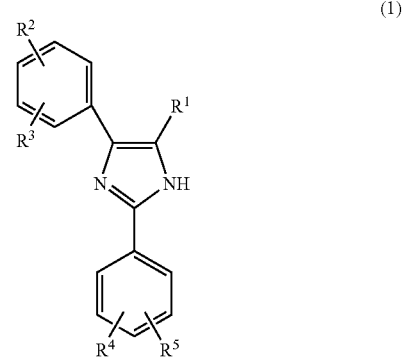

wherein $R^1$ is hydrogen or methyl, and either $R^2$ and $R^3$ represent chlorine and $R^4$ and $R^5$ represent hydrogen, or $R^2$ and $R^3$ represent hydrogen and $R^4$ and $R^5$ represent chlorine.

Item 2. A composition according to Item 1 wherein the compound represented by general formula (1) is one wherein $R^1$ is methyl.

Item 3. A composition according to Item 1 wherein the compound represented by general formula (1) is one wherein $R^2$ and $R^3$ represent hydrogen and $R^4$ and $R^5$ represent chlorine.

Item 4. A composition according to Item 3 wherein the compound represented by general formula (1) is at least one member selected from the group consisting of 2-(2,3-dichlorophenyl)-4-phenyl-5-methylimidazole and 2-(2,4-dichlorophenyl)-4-phenyl-5-methylimidazole.

Item 5. A composition according to Item 1 wherein the compound represented by general formula (1) is one wherein $R^2$ and $R^3$ represent chlorine and $R^4$ and $R^5$ represent hydrogen.

Item 6. A composition according to Item 5 wherein the compound represented by general formula (1) is at least one member selected from the group consisting of 2-phenyl-4-(2, 4-dichlorophenyl)-5-methylimidazole and 2-phenyl-4-(3,4-dichlorophenyl)-5-methylimidazole.

Item 7. A composition according to Item 1 wherein the compound represented by general formula (1) is present in an amount of 0.01 to 10% by weight based on the whole composition.

Item 8. A water-based composition for treating copper or copper alloy surfaces for lead-free soldering, the composition comprising an acid and an imidazole compound represented by general formula (1):

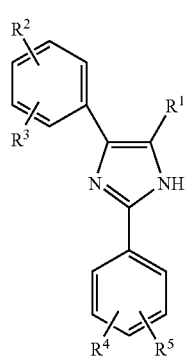

(1)

wherein $R^1$ is hydrogen or methyl, and either $R^2$ and $R^3$ represent chlorine and $R^4$ and $R^5$ represent hydrogen, or $R^2$ and $R^3$ represent hydrogen and $R^4$ and $R^5$ are chlorine.

Item 9. A water-based composition according to Item 8, wherein the acid is at least one member selected from the group consisting of $C_1$-$C_{12}$ saturated or unsaturated aliphatic monocarboxylic acid, $C_2$-$C_6$ saturated or unsaturated aliphatic dicarboxylic acids, $C_7$ or $C_8$ aromatic carboxylic acids, $C_6$-$C_8$ aromatic sulfonic acids, hydrochloric acid, phosphoric acid, sulfuric acid and nitric acid.

Item 10. A water-based composition according to Item 8 wherein the imidazole compound represented by general formula (1) is present in an amount of 0.01 to 10% by weight based on the whole composition and the acid is present in an amount of 0.1 to 50% by weight based on the whole composition, and wherein the acid is at least one member selected from the group consisting of $C_1$-$C_{12}$ saturated or unsaturated aliphatic monocarboxylic acids, $C_2$-$C_6$ saturated or unsaturated aliphatic dicarboxylic acids, $C_7$ or $C_8$ aromatic carboxylic acids, $C_6$-$C_8$ aromatic sulfonic acids, hydrochloric acid, phosphoric acid, sulfuric acid and nitric acid.

Item 11. A water-based composition according to Item 8 further comprising a copper compound.

Item 12. A water-based composition according to Item 11 wherein the copper compound is at least one member selected from the group consisting of copper halides, copper salts of acids and copper hydroxide.

Item 13. A water-based composition according to Item 11 wherein the copper compound is at least one member selected from the group consisting of copper halides, copper salts of acids and copper hydroxide, and is contained in an amount of 0.01 to 10% by weight based on the whole composition.

Item 14. A water-based composition according to Item 8 further comprising a zinc compound.

Item 15. A water-based composition according to Item 14, wherein the zinc compound is at least one member selected from the group consisting of zinc oxide and zinc salts of acids.

Item 16. A water-based composition according to Item 14, wherein the zinc compound is at least one member selected from the group consisting of zinc oxide and zinc salts of acids and the content of the zinc compound is 0.01 to 10% by weight based on the whole composition.

Item 17. A water-based composition according to Item 8 further comprising a halogen compound.

Item 18. A water-based composition according to Item 17 wherein the halogen compound is at least one member selected from the group consisting of alkali metal halides and ammonium halides.

Item 19. A water-based composition according to Item 17 wherein the halogen compound is at least one member selected from the group consisting of alkali metal halides and ammonium halides and the content of the halogen compound is 0.001 to 1% by weight based on the whole composition.

Item 20. A water-based composition according to Item 8 further comprising an organic solvent.

Item 21. A water-based composition according to Item 20 wherein the organic solvent is at least one member selected from the group consisting of lower alcohols, acetone, N,N-dimethylformamide, ethyleneglycol and glycol ethers.

Item 22. A water-based composition according to Item 20 wherein the organic solvent is at least one member selected from the group consisting of lower alcohols, acetone, N,N-dimethylformamide, ethyleneglycol and glycol ethers, and the content of the organic solvent is 1 to 50% by weight based on the whole composition.

Item 23. A process for treating copper or copper alloy surfaces for lead-free soldering, the process comprising contacting a copper or copper alloy-containing material with the water-based composition according to any one of Items 1 to 22.

Item 24. A soldering process comprising contacting a copper or copper alloy-containing material with the water-based composition according to any one of Items 1 to 22 and soldering the copper or copper alloy-containing material using lead-free solder.

Item 25. Use of a compound represented by general formula (1):

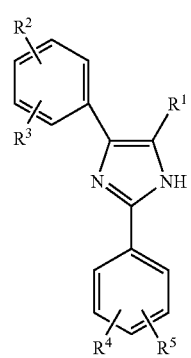

(1)

wherein $R^1$ is hydrogen or methyl, and either $R^2$ and $R^3$ represent chlorine and $R^4$ and $R^5$ represent hydrogen, or $R^2$ and $R^3$ represent hydrogen and $R^4$ and $R^5$ represent chlorine, as an agent for treating copper or copper alloy surfaces for lead-free soldering.

Item 26. Use according to Item 25 wherein the compound represented by general formula (1) is one wherein $R^1$ is methyl.

Item 27. Use according to Item 25 wherein the compound represented by general formula (1) is one wherein $R^2$ and $R^3$ represent hydrogen and $R^4$ and $R^5$ represent chlorine.

Item 28. Use according to Item 27 wherein the compound represented by general formula (1) is at least one member selected from the group consisting of 2-(2,3-dichlorophenyl)-4-phenyl-5-methylimidazole and 2-(2,4-dichlorophenyl)-4-phenyl-5-methylimidazole.

Item 29. Use according to Item 25 wherein the compound represented by general formula (1) is one wherein $R^2$ and $R^3$ represent chlorine and $R^4$ and $R^5$ represent hydrogen.

Item 30. Use according to Item 29 wherein the compound represented by general formula (1) is at least one member selected from the group consisting of 2-phenyl-4-(2,4-dichlorophenyl)-5-methylimidazole and 2-phenyl-4-(3,4-dichlorophenyl)-5-methylimidazole.

Item 31. An imidazole compound represented by general formula (1):

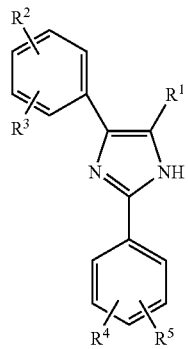

(1)

wherein $R^1$ is hydrogen or methyl, and either $R^2$ and $R^3$ represent chlorine and $R^4$ and $R^5$ represent hydrogen, or $R^2$ and $R^3$ represent hydrogen and $R^4$ and $R^5$ represent chlorine, with the proviso that 2-(2,4-dichlorophenyl)-4-phenyl-5-methylimidazole is excluded.

Item 32. A compound according to Item 31 wherein $R^1$ is methyl.

Item 33. A compound according to Item 31 wherein $R^2$ and $R^3$ represent hydrogen, and $R^4$ and $R^5$ represent chlorine.

Item 34. A compound according to Item 33, which is 2-(2,3-dichlorophenyl)-4-phenyl-5-methylimidazole.

Item 35. A compound according to Item 31 wherein $R^2$ and $R^3$ represent chlorine, and $R^4$ and $R^5$ represent hydrogen.

Item 36. A compound according to Item 35, which is 2-phenyl-4-(2,4-dichlorophenyl)-5-methylimidazole or 2-phenyl-4-(3,4-dichlorophenyl)-5-methylimidazole.

The imidazole compound of the present invention can form a chemical layer with excellent heat-resistance on copper or copper alloy surfaces when used as a surface treatment agent for copper or copper alloy constituting a circuit part, etc., of a printed wiring board. Moreover, wettability of lead-free solders on the surfaces can be remarkably improved, and thus good solderability with lead-free solder can be attained.

The imidazole compound of the invention is suitable for use in the process of lead-free soldering, and thus is useful from the standpoint of environmental protection.

These compounds are also useful as epoxy resin curing agents and drug intermediates.

DETAILED DESCRIPTION OF THE INVENTION

Hereinafter, the present invention will be described in more detail.

(A) Imidazole Compound

The imidazole compounds of the invention are novel compounds which have not been disclosed in any references, and represented by general formula (1):

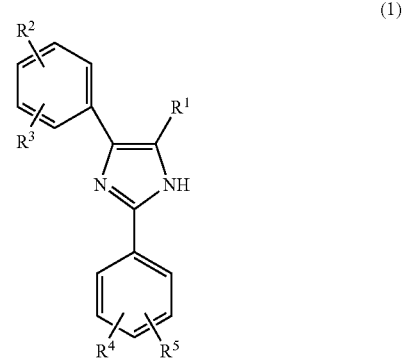

(1)

wherein $R^1$ is hydrogen or methyl, and either $R^2$ and $R^3$ represent chlorine and $R^4$ and $R^5$ represent hydrogen, or $R^2$ and $R^3$ represent hydrogen and $R^4$ and $R^5$ represent chlorine, with the proviso that 2-(2,4-dichlorophenyl)-4-phenyl-5-methylimidazole is excluded.

The imidazole compounds of the present invention are classified into 2-phenyl-4-(dichlorophenyl)imidazole compounds represented by general formula (2)

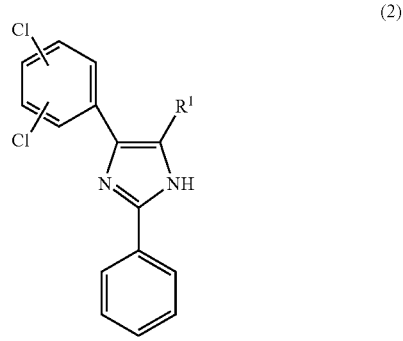

(2)

wherein $R^1$ is as defined above, and 2-(dichlorophenyl)-4-phenylimidazole compounds (excluding 2-(2,4-dichlorophenyl)-4-phenyl-5-methylimidazole) represented by general formula (3):

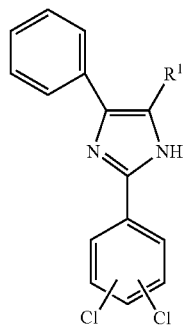

(3)

wherein R¹ is as defined above.

2-phenyl-4-(dichlorophenyl)imidazole compounds represented by the above-described general formula (2) include the following:
2-phenyl-4-(2,3-dichlorophenyl)imidazole,
2-phenyl-4-(2,4-dichlorophenyl)imidazole,
2-phenyl-4-(2,5-dichlorophenyl)imidazole,
2-phenyl-4-(2,6-dichlorophenyl)imidazole,
2-phenyl-4-(3,4-dichlorophenyl)imidazole,
2-phenyl-4-(3,5-dichlorophenyl)imidazole,
2-phenyl-4-(2,3-dichlorophenyl)-5-methylimidazole,
2-phenyl-4-(2,4-dichlorophenyl)-5-methylimidazole,
2-phenyl-4-(2,5-dichlorophenyl)-5-methylimidazole,
2-phenyl-4-(2,6-dichlorophenyl)-5-methylimidazole,
2-phenyl-4-(3,4-dichlorophenyl)-5-methylimidazole and
2-phenyl 4-(3,5-dichlorophenyl)-5-methylimidazole.

2-(dichlorophenyl)-4-phenylimidazole compounds represented by the above-mentioned general formula (3) include the following:
2-(2,3-dichlorophenyl)-4-phenylimidazole,
2-(2,4-dichlorophenyl)-4-phenylimidazole,
2-(2,5-dichlorophenyl)-4-phenylimidazole,
2-(2,6-dichlorophenyl)-4-phenylimidazole,
2-(3,4-dichlorophenyl)-4-phenylimidazole,
2-(3,5-dichlorophenyl)-4-phenylimidazole,
2-(2,3-dichlorophenyl)-4-phenyl-5-methylimidazole,
2-(2,5-dichlorophenyl)-4-phenyl-5-methylimidazole,
2-(2,6-dichlorophenyl)-4-phenyl-5-methylimidazole,
2-(3,4-dichlorophenyl)-4-phenyl-5-methylimidazole and
2-(3,5-dichlorophenyl)-4-phenyl-5-methylimidazole.

Among the 2-phenyl-4-(dichlorophenyl)imidazole compounds, 2-phenyl-4-(dichlorophenyl)-5-methylimidazole compounds, which have a methyl group at the 5-position of the imidazole ring, are preferred when good solderability, and additionally availability of starting materials and ease of synthesis are taken into consideration, and 2-phenyl-4-(2,4-dichlorophenyl)-5-methylimidazole and 2-phenyl-4-(3,4-dichlorophenyl)-5-methylimidazole are particularly preferred.

Among the 2-(dichlorophenyl)-4-phenylimidazole compounds, when good solderability and additionally ease of availability of starting materials and ease of synthesis are taken into consideration, 2-(dichlorophenyl)-4-phenyl-5-methylimidazole compounds, which have methyl group at the 5-position of the imidazole ring, are preferred, and in particular 2-(2,3-dichlorophenyl)-4-phenyl-5-methylimidazole is more preferred.

Process for Producing 2-phenyl-4-(dichlorophenyl) Imidazole Compounds Represented by General Formula (2)

2-phenyl-4-(dichlorophenyl)imidazole compounds can be synthesized according to a known process. More specifically, as shown in the following reaction scheme (5), a dichlorophenyl alkylketone compound halogenated at the 2-position and a benzamidine compound (typified by the benzamidine illustrated in the reaction scheme (5)) are reacted with heating in an organic solvent in the presence of a dehalogenation agent, giving a 2-phenyl-4-(dichlorophenyl)imidazole compound.

Reaction Scheme (5)

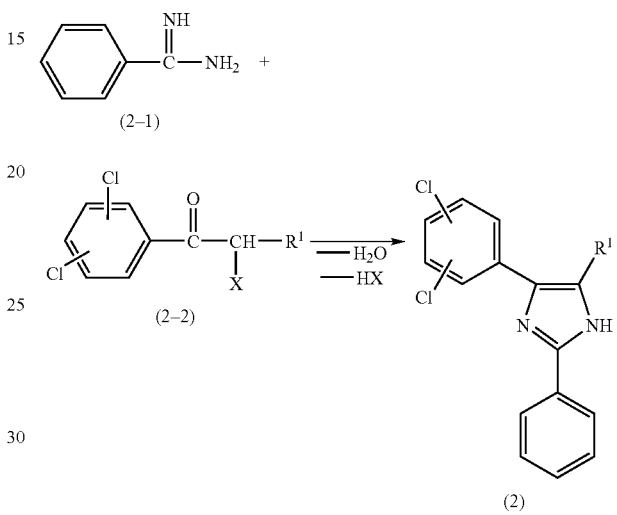

wherein R¹ is hydrogen or methyl, and X is chlorine, bromine or iodine.

More specifically, a dichlorophenyl alkyl ketone compound halogenated at the 2-position (2-2) is reacted with a benzamidine compound (2-1) used in an amount of about 0.8 to about 1.5 moles, and preferably about 0.9 to about 1.1 moles, per mole of compound (2-2), in the presence of a dehydrohalogenation agent used in an amount of about 1 to about 10 moles per mole of compound (2-2) in a solvent at room temperature to reflux temperature for about 1 to about 10 hours, giving a 2-phenyl-4-(dichlorophenyl)imidazole compound. The reaction may be usually carried out at atmospheric pressure.

Subsequently, the crude solid 2-phenyl-4-(dichlorophenyl) imidazole compound can be obtained by adding a large amount of water to the obtained reaction solution or a concentrate obtained by evaporating the solvent. This crude product can be purified by recrystallization.

Typical dichlorophenyl alkyl ketone compounds halogenated at the 2-position (2-2) for use in the production of 2-phenyl-4-(dichlorophenyl)imidazole compounds of the present invention include, 2,2',3'-trichloroacetophenone, 2,2', 4'-trichloroacetophenone, 2-bromo-2',5'-dichloroacetophenone, 2-iodo-2',6'-dichloro acetophenone, 2-bromo-3',4'-dichloroacetophenone, 2-bromo-3',5'-dichloroacetophenone, 2-bromo-2',3'-dichloropropiophenone, 2,2',4'-trichloropropiophenone, 2-bromo-2',5'-dichloropropiophenone, 2-bromo-2',6'-dichloropropiophenone, 2-bromo-3',4'-dichloropropiophenone, 2-iodo-3',5'-dichloropropiophenone, etc.

Among the dichlorophenyl alkyl ketone compounds halogenated at the 2-position, 2,2',4'-trichloroacetophenone can be commercially available as a reagent and the others can be synthesized by halogenating the 2-position of a dichlorophenyl alkyl ketone. For halogenation of the 2-position thereof, 2-position chlorination and 2-position iodination can be adopted, but 2-position bromination using bromine is the simplest. More specifically, 1 mole of bromine is reacted with 1 mole of a dichlorophenyl alkyl ketone such as dichloroacetophenone or dichloropropiophenone, whereby a dichlorophenyl alkylketone compound halogenated at the 2-position can be easily produced.

Benzamidine compounds include benzamidine, organic acid salts of benzamidine such as benzamidine acetate and inorganic acid salts of benzamidine such as benzamidine hydrochloride, etc.

Any known dehydrohalogenation agent can be used without limitation. Examples of such known dehydrohalogenation agents include inorganic bases such as sodium hydroxide, potassium hydroxide, calcium hydroxide, sodium carbonate, potassium carbonate, sodium bicarbonate and potassium bicarbonate; organic bases such as triethylamine, 1,8-diazabicyclo[5,4,0]-7-undecene (DBU); and metal alkoxides such as sodium methoxide and potassium t-butoxide, etc.

Any known solvents can be used that can dissolve the dichlorophenyl alkyl ketone compound halogenated at the 2-position and the benzamidine compound and that are inert to the reaction. Such solvents include, for example, alcohols such as ethanol and isopropyl alcohol; hydrocarbons such as hexane and toluene; halogenated hydrocarbons such as chloroform and chlorobenzene; esters such as ethyl acetate; nitrites such as acetonitrile; ethers such as tetrahydrofuran and dioxane; amides such as dimethylformamide (DMF) and dimethylacetamide (DMAC); dimethyl sulfoxide (DMSO), etc.

Process for Producing 2-(dichlorophenyl)-4-phenylimidazole Compounds Represented By General Formula (3)

Among 2-(dichlorophenyl)-4-phenylimidazole compounds of the present invention, 2-(dichlorophenyl)-4-phenylimidazole compounds (3H), in which the 5-position of the imidazole ring is unsubstituted, are obtained by heating 2-acetoxyacetophenone (3-1), a dichlorobenzaldehyde compound (3-2), ammonia and copper (II) acetate to effect reaction in an alcohol, as shown in the following reaction scheme (6):

Reaction Scheme (6)

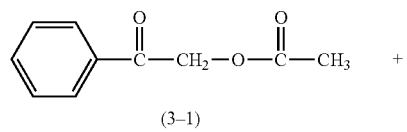
(3-1)

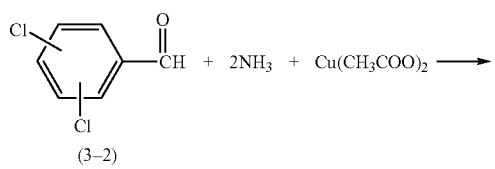

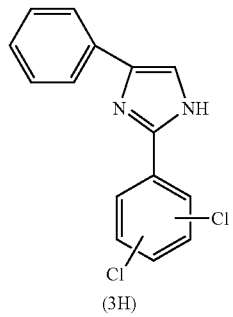
(3H)

In the reaction shown in the reaction scheme (6), 2-acetoxyacetophenone (3-1) may be used in an amount of about 0.8 to about 1.5 moles, and preferably about 0.9 to about 1.1 moles, per mole of dichlorobenzaldehyde compound (3-2). Ammonia may be used in an amount of about 10 to about 50 moles, and preferably about 20 to about 30 moles, per mole of dichlorobenzaldehyde compound (3-2). Copper (II) acetate may be used in an amount of about 1 to about 5 moles, and preferably about 2 to about 3 moles per mole of dichlorobenzaldehyde compound (3-2).

2-Acetoxy acetophenone (3-1) can be obtained by reacting 2-chloroacetophenone with acetic acid and potassium acetate (see Reference Example 1 described below). Usable dichlorobenzaldehyde compounds (3-2) include 2,3-dichlorobenzaldehyde, 2,4-dichlorobenzaldehyde, 2,5-dichlorobenzaldehyde, 2,6-dichlorobenzaldehyde, 3,4-dichlorobenzaldehyde or 3,5-dichlorobenzaldehyde. These compounds are known and can be readily available. Alcohols as reaction solvent are methanol, ethanol, propanol, isopropanol, etc.

The reaction temperature may be usually from about 50 to about 80° C. and the reaction time may be usually about 1 to about 10 hours. The reaction is usually carried out at atmospheric pressure.

After completion of the heating, the precipitate is filtered off and is then suspended in methanol. Subsequently, sodium hydrosulfide, used in an amount of about 0.5 to about 0.8 moles per mole of dichlorobenzaldehyde compound (3-2), is added to this methanol suspension in small portions until the completion of consumption. The copper sulfide precipitated is removed by filtration, the methanol is evaporated off under reduced pressure, and the residue is then washed with water, giving crude 2-(dichlorophenyl)-4-phenylimidazole compound (3H) as a solid. The crude product can be purified by recrystallization.

2-(Dichlorophenyl)-4-phenyl-5-methylimidazole compounds (3M) substituted, which have a methyl group at the 5-position of the imidazole ring, are obtained by heating a dichlorobenzaldehyde compound (3-2), 1-phenyl-1,2-propanedione (3-3) and ammonium acetate to effect reaction in acetic acid, as shown in the following reaction scheme (7).

Reaction Scheme (7)

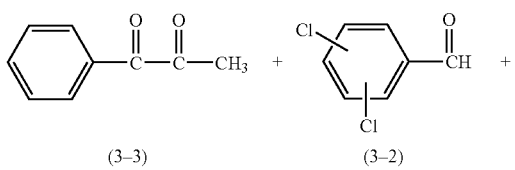
(3-3)     (3-2)

-continued $2CH_3CO_2NH_4 \xrightarrow[-3H_2O]{CH_3CO_2H}$ 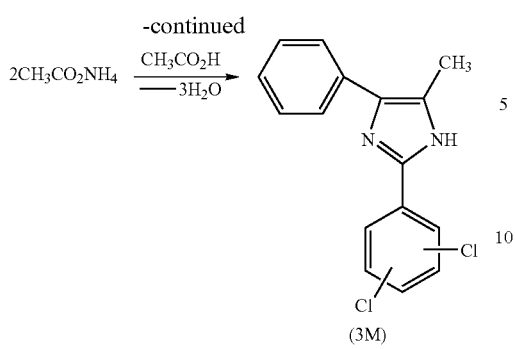

(3M)

In the reaction shown in the reaction scheme (7), 1-phenyl-1,2-propanedione (3-3) may be used in an amount of about 0.8 to about 1.5 moles, and preferably about 0.9 to about 1.1 moles, per mole of dichlorobenzaldehyde compound (3-2). Ammonium acetate may be used in an amount of about 2 to about 10 moles, and preferably about 4 to about 6 moles, per mole of dichlorobenzaldehyde compound (3-2).

The reaction temperature may be usually 80° C. or above, and preferably about reflux temperature, and the reaction time may be from about 1 to about 10 hours. The reaction can be usually carried out at an atmospheric pressure.

After the heating is complete, the reaction solution or a residue obtained by evaporating the acetic acid from the reaction solution is mixed with an aqueous solution containing an excess, with respect to the acetic acid contained in the residue, of alkali agents such as sodium hydroxide, sodium carbonate, ammonia, etc., in such a manner that the amount (by weight) of said aqueous solution is 5 to 20 times the amount of the residue, whereby crude 2-(dichlorophenyl)-4-phenyl-5-methylimidazole compounds (3M) can be obtained as a solid precipitate. The solid collected by filtration can be purified by recrystallization.

(B) Water-Based Surface Treatment Composition for Copper or Copper Alloys

An imidazole compound represented by general formula (1):

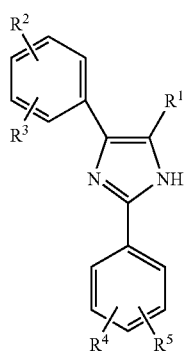

(1)

wherein $R^1$ is hydrogen or methyl, and either $R^2$ and $R^3$ represent chlorine and $R^4$ and $R^5$ represent hydrogen, or $R^2$ and $R^3$ represent hydrogen and $R^4$ and $R^5$ represent chlorine, can be suitably used as a component, in particular as an active ingredient, of a water-based surface treatment composition for copper or copper alloys for lead-free soldering. More specifically, the composition of the present invention is an aqueous composition for treating copper or copper alloy surfaces for lead-free soldering and contains the compound represented by the above-mentioned general formula (1).

The compounds represented by the above-described general formula (1) in the compositions of the present invention include 2-phenyl-4-(dichlorophenyl)imidazole compounds represented by general formula (2):

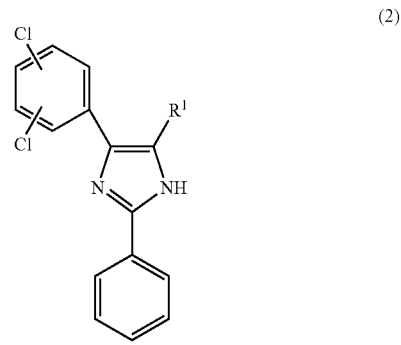

(2)

wherein $R^1$ is as defined above and
2-(dichlorophenyl)-4-phenylimidazole compounds represented by general formula (3):

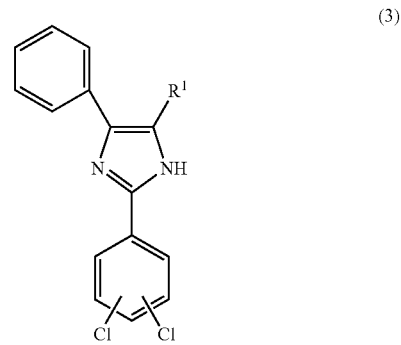

(3)

wherein $R^1$ is as defined above. One or more of the compounds represented by the above-mentioned general formula (1) may be contained in the composition of the invention.

The 2-phenyl-4-(dichlorophenyl)imidazole compounds the among the compounds represented by the above-mentioned general formula (1) include the following:
2-phenyl-4-(2,3-dichlorophenyl)imidazole,
2-phenyl-4-(2,4-dichlorophenyl) imidazole,
2-phenyl-4-(2,5-dichlorophenyl)imidazole,
2-phenyl-4-(2,6-dichlorophenyl)imidazole,
2-phenyl-4-(3,4-dichlorophenyl)imidazole,
2-phenyl-4-(3,5-dichlorophenyl) imidazole,
2-phenyl-4-(2,3-dichlorophenyl)-5-methylimidazole,
2-phenyl-4-(2,4-dichlorophenyl)-5-methylimidazole,
2-phenyl-4-(2,5-dichlorophenyl)-5-methylimidazole,
2-phenyl-4-(2,6-dichlorophenyl)-5-methylimidazole,
2-phenyl-4-(3,4-dichlorophenyl)-5-methylimidazole, and
2-phenyl-4-(3,5-dichlorophenyl)-5-methylimidazole.

The 2-(dichlorophenyl)-4-phenylimidazole compounds among the compounds represented by the above-mentioned general formula (1) include the following:
2-(2,3-dichlorophenyl)-4-phenylimidazole,
2-(2,4-dichlorophenyl)-4-phenylimidazole,
2-(2,5-dichlorophenyl)-4-phenylimidazole,
2-(2,6-dichlorophenyl)-4-phenylimidazole, 2-(3,4-dichlorophenyl)-4-phenylimidazole,
2-(3,5-dichlorophenyl)-4-phenylimidazole,
2-(2,3-dichlorophenyl)-4-phenyl-5-methylimidazole,
2-(2,4-dichlorophenyl)-4-phenyl-5-methylimidazole,
2-(2,5-dichlorophenyl)-4-phenyl-5-methylimidazole,
2-(2,6-dichlorophenyl)-4-phenyl-5-methylimidazole,
2-(3,4-dichlorophenyl)-4-phenyl-5-methylimidazole, and
2-(3,5-dichlorophenyl)-4-phenyl-5-methylimidazole.

These imidazole compounds are characterized by having a basic skeleton of 2,4-diphenylimidazole compound in which phenyl group is bonded to the 2- and 4-positions of the imidazole ring, and the phenyl group at the 2- or 4-position is substituted with two chlorine atoms.

Among the 2-phenyl-4-(dichlorophenyl)imidazole compounds represented by general formula (2), 2-phenyl-4-(dichlorophenyl)-5-methylimidazole compounds, which have a methyl group at the 5-position of the imidazole ring, are preferred in view of good solder flow-up rate and solder spreadability which are mentioned later and ease of dissolution into water. Among them, 2-phenyl-4-(2,4-dichlorophenyl)-5-methylimidazole and 2-phenyl-4-(3,4-dichlorophenyl)-5-methylimidazole are more preferred.

Among the 2-(dichlorophenyl)-4-phenylimidazole compounds represented by general formula (3), 2-(dichlorophenyl)-4-phenyl-5-methylimidazole compounds, which have a methyl group at the 5-position of the imidazole ring, preferred in view of good solder flow-up rate, good solder spreadability and ease of dissolution into water. Among them, 2-(2,3-dichlorophenyl)-4-phenyl-5-methylimidazole and 2-(2,4-dichlorophenyl)-4-phenyl-5-methylimidazole are particularly preferred.

The aqueous compositions of the present invention preferably contain an acid in addition to an imidazole compound represented by the above-mentioned general formula (1).

The above-mentioned imidazole compound may be contained in the water-based composition in an amount of about 0.01 to about 10% by weight, and preferably about 0.1 to about 5% by weight, based on the whole composition. When the content of imidazole compound is within the above-mentioned range, a chemical layer with a thickness sufficient for practical use can be formed on the copper surface to thereby sufficiently protect the copper surface from oxidation, and the composition is in the form of a clear or uniform solution in which the imidazole compound does not remain undissolved.

The composition of the present invention preferably contains an organic acid or an inorganic acid so that an imidazole compound can be dissolved in water. Examples of typical organic acids include $C_1$-$C_{12}$ (more preferably, $C_1$ to $C_3$) saturated or unsaturated aliphatic monocarboxylic acids such as formic acid, acetic acid, propionic acid, butyric acid, heptanoic acid, caprylic acid, capric acid, lauric acid, glycolic acid, lactic acid and acrylic acid; $C_2$-$C_6$ saturated or unsaturated aliphatic dicarboxylic acids such as oxalic acid, succinic acid, maleic acid, fumaric acid, tartaric acid and adipic acid; $C_7$ or $C_8$ aromatic carboxylic acids such as benzoic acid, p-nitrobenzoic acid and salicylic acid; $C_6$-$C_8$ aromatic sulfonic acids such as p-toluene sulfonic acid; picric acid etc. Inorganic acid includes hydrochloric acid, phosphoric acid, sulfuric acid, nitric acid, etc.

Among the above acids, organic acids are preferred, and $C_1$-$C_{12}$ saturated or unsaturated aliphatic monocarboxylic acids are especially preferred, and formic acid, acetic acid, propionic acid and lactic acid are particularly preferable since the organic acids react with the basic imidazole compound to generate a salt, whereby the imidazole compound can be easily dissolved in water, and the organic acids also function as an organic solvent. Acids can be used singly or in combination.

The acid is used in an amount effective for dissolving the compound represented by general formula (1) in water. More specifically, the amount of the acid to be used is preferably about 0.1 to about 50% by weight, and more preferably about 1 to about 40% by weight, based on the whole composition. The acid content within the above-mentioned range attains the following effects: the imidazole compound can be sufficiently dissolved in water; the deterioration of work environment due to odor is avoided; and the difficulty of handling due to increased corrosiveness of the water-based composition is avoided.

If necessary, a small amount of organic solvent may be included in addition to the acid in order to dissolve the imidazole compound in water. Any organic solvents that are freely miscible with water can be used. Such organic solvents include lower alcohols such as methanol, ethanol, isopropyl alcohol, etc.; acetone, N,N-dimethylformamide, ethylene glycol, glycol ethers, etc.

Among the above organic solvents, ethylene glycol and glycol ethers are preferred from the standpoint of facilitating dissolution of the imidazole compound in water. Such organic solvents can be used singly or in combination.

The composition of the present invention may or may not contain the organic solvent. The organic solvent, when contained in the composition, is used in an amount effective for dissolving the compound represented by general formula (1) in water. Typically, the amount is preferably about 1 to about 50% by weight, more preferably about 1 to about 40% by weight, based on the whole composition. When the amount is within the above-mentioned range, the organic solvent can sufficiently dissolve the imidazole compound, and does not increase hazards of the water-based composition such as inflammability, combustibility, etc.

If desired, a copper compound may be added to the composition of the invention so as to increase the rate of a chemical layer formation on the copper or copper alloy surfaces.

Any known copper compounds can be used without restriction. Representative examples of the known copper compounds include copper halides such as copper (I) chloride, copper (II) chloride, copper (I) bromide, copper (II) bromide and copper iodide; copper salts of acids such as copper acetate, copper phosphate, copper sulfate and copper nitrate; copper hydroxide, etc. Among these, copper halides and copper salts are preferred.

Copper compounds can be used singly or in combination. A copper compound need not be used, but when used, should be added to the composition in an amount effective for increasing the rate of forming a chemical layer on the surface of copper or copper alloy. Typically, the amount is preferably about 0.01 to about 10% by weight, more preferably about 0.02 to about 5% by weight based on the whole composition. A copper compound used in an amount within the above-mentioned range can sufficiently improve the chemical layer formation rate and avoid precipitation of the imidazole compound due to salting-out effect.

If necessary, the composition of the present invention can contain a zinc compound, so as to improve the heat-resistance of the chemical layer formed. Any known water-soluble zinc compounds can be used. Representative examples of the zinc compound include zinc oxide; and zinc salts of acids such as zinc formate, zinc acetate, zinc oxalate, zinc lactate, zinc citrate, zinc chloride, zinc sulfate, zinc nitrate and zinc phosphate. Among these, zinc formate, zinc acetate and zinc chloride are preferred.

Zinc compounds can be used singly or in combination. A zinc compound may or may not be contained in the composition, but when present, should be used in an amount effective for improving the heat resistance of the chemical layer. Typically, the amount is preferably about 0.01 to about 10% by weight, more preferably about 0.02 to about 5% by weight, based on the whole composition. Zinc compounds added in an amount within the above-described range can sufficiently improve heat-resistance of a chemical layer, and avoid precipitation of the imidazole compound due to salting-out.

When a copper compound or zinc compound is used, it is desirable to add, in addition to an organic or inorganic acid, a basic substance having a buffering action so as to stabilize the pH of the solution. Such basic substances include amines such as ammonia and organic amines and alkali or alkaline-earth metal hydroxides such as sodium hydroxide, potassium hydroxide, magnesium hydroxide, etc. It is desirable to maintain the pH of the composition at about 1 to about 6 by adding such basic substances. More specifically, it is preferable to use the above-mentioned basic substances in an amount effective for maintaining the pH of the composition in the above-mentioned range.

The surface treatment composition of the invention may contain a halogen compound for further improving the chemical layer formation rate and the heat resistance thereof. Such halogen compounds include alkali metal halides and ammonium halides. Examples are fluorine compounds such as sodium fluoride, potassium fluoride and ammonium fluoride; chlorine compounds such as sodium chloride, potassium chloride and ammonium chloride; bromine compounds such as sodium bromide, potassium bromide and ammonium bromide; and iodine compounds such as sodium iodide, potassium iodide and ammonium iodide, and the like.

Among such halogen compounds, chlorine compounds, bromine compounds and iodine compounds are preferred. Halogen compounds can be used singly or in combination. The composition of the invention may or may not contain the halogen compound. The halogen compound, when present, is used in an amount effective for increasing the chemical layer formation rate and the heat resistance thereof. Typically, the amount is preferably about 0.001 to about 1% by weight, more preferably about 0.01 to about 0.1% by weight, based on the whole composition. Halogen compound added in an amount within the above-described range can sufficiently improve the rate of chemical layer formation and the heat-resistance thereof, and avoid precipitation of the imidazole compound due to salting-out.

(D) Surface Treatment Method

The surface-treatment method of the invention comprises contacting a copper or copper alloy-containing material with the above-mentioned water-based composition of the invention.

Representative examples of the copper or copper alloy-containing material include a circuit part of a printed wiring board, a circuit part of electronic components, such as a IC package, etc. The kind of copper alloy is not limited, and includes, for example, brass, tin bronze, phosphorus bronze, etc.

The composition of the invention is contacted with copper or copper-alloy material at a temperature and a time effective for forming a chemical layer thereon. Typically, the liquid temperature of the composition of the present invention is usually about 10 to about 70° C., and preferably about 20 to about 50° C., and the contact time is about 1 second to about 10 minutes, and preferably about 10 seconds to about 5 minutes. The contact method is not limited, and includes, dipping, spraying, spreading, etc. After this contact process, the copper or copper alloy-containing material is washed with water, dried and subjected to soldering.

(E) Soldering Method

The soldering method of the invention comprises contacting the copper or copper alloy-containing material with the water-based composition of the invention and soldering the copper or copper alloy-containing material using lead-free solder.

The process of contacting the water-based composition is described above. A chemical layer is formed on the surface of the copper or copper alloy-containing material by contacting the water-based composition of the invention with the copper or copper alloy-containing material, followed by drying.

The present invention includes two kinds of soldering methods: one method comprising connecting electronic components such as discrete parts using lead-free solder to a copper through-hole part of a printed wiring board and the other method comprising connecting electronic components such as chip type parts, an IC package, etc., to the surface of a copper pad of a printed wiring board using lead-free solder.

Soldering between the copper or copper alloy-containing material and the electronic components, etc. may be conducted by a known method. The method of soldering electronic components to a circuit part of a printed wiring board is described below in detail. Soldering methods include flow soldering methods and reflow soldering methods. Flow soldering comprises moving a printed wiring board over a molten liquid-state solder in a solder bath for soldering junctions between electronic components and the printed wiring board. In contrast, reflow soldering comprises printing in advance a solder paste on the printed wiring board according to a circuit pattern, mounting electronic components thereon, and heating the whole printed wiring board to melt the solder to complete the soldering.

Any known lead-free solder can be used. Examples of such known lead-free solders include Sn—Ag—Cu-based solders, Sn—Ag—Bi-based solders, Sn—Bi-based solders, Sn—Ag—Bi—In-based solders, Sn—Zn-based solders, Sn—Cu-based solders, etc. In particular, Sn—Ag—Cu-based solders are preferred.

After surface treatment process of the invention but before the soldering process, a thermoplastic resin film may be formed on the chemical layer formed through the surface treatment to obtain a double layer structure, which further improves heat-resistance.

The thermoplastic resin film is formed as follows. For example, a chemical layer is formed on the surface of copper or copper alloy, and thereafter a thermoplastic resin with excellent heat-resistance composed of rosin derivatives such as rosin and rosin esters; terpene resin derivatives such as terpene resins and terpene phenol resins; aromatic hydrocarbon resins, aliphatic hydrocarbon resins, alicyclic hydrocarbon resins, or mixtures thereof, is dissolved in a solvent such as toluene, ethyl acetate, isopropyl alcohol, etc., and the solution is uniformly applied to the chemical layer with a roll coater, etc., so that the film thickness after drying is about 1 to about 30 μm, to obtain a double layered structure composed of the chemical layer and the thermoplastic resin.

In this case, the soldering method of the invention comprises a surface treatment step in which a chemical layer is formed on the surface of the copper or copper alloy-containing material by contacting the copper or copper alloy-containing material with the water-based composition of the invention, a step of forming a thermoplastic resin film on the chemical layer, and a step of soldering the copper or copper-alloy material on which the thermoplastic resin film is formed.

EXAMPLES

Hereinafter, the present invention will be described in detail with reference to Examples and Experimental Examples, but is not limited thereto.

First, Examples 1-1 to 1-4, in which 2-phenyl-4-(dichlorophenyl)imidazole compounds were produced, will be described. Starting materials used in each Example were obtained as given below.

Starting Material

2',4'-dichloroacetophenone (manufactured by Tokyo Kasei Kogyo Co., Ltd., reagent)

3',4'-dichloroacetophenone (manufactured by Tokyo Kasei Kogyo Co., Ltd., reagent)

2',4'-dichloropropiophenone (manufactured by Lancaster, reagent)

3',4'-dichloropropiophenone (manufactured by Aldrich, reagent)

benzamidine hydrochloride (manufactured by Tokyo Kasei Kogyo Co., Ltd., reagent)

Example 1-1

Synthesis of 2-phenyl-4-(2,4-dichlorophenyl)imidazole 43.4 g (0.267 mol) of bromine was added dropwise to a solution of 50.5 g (0.267 mol) of 2',4'-dichloroacetophenone in 100 g of methanol at a reaction temperature of 45 to 50° C. After the addition was complete, the methanol was evaporated off from the reaction solution under reduced pressure. The resultant concentrate was dissolved in 120 g of toluene and was then washed with water (100 ml×3 times). Thereafter, the toluene was distilled off under reduced pressure, giving 68.0 g (0.254 mol) of crude brown oily 2-bromo-2',4'-dichloroacetophenone.

A suspension of 39.8 g (0.254 mol) of benzamidine hydrochloride and 13.7 g (0.254 mol) of sodium methylate in 170 ml of tetrahydrofuran was heated under reflux for 1 hour, and cooled to 25° C. A solution of 68.0 g (0.254 mol) of the above-mentioned crude 2-bromo-2',4'-dichloroacetophenone in 120 ml of tetrahydrofuran was added dropwise in such a manner that the reaction temperature did not exceed 30° C. After the addition was complete, 13.7 g (0.254 mol) of sodium methylate was added, and the mixture was heated under reflux for 1 hour. Subsequently, the reaction solution was cooled to room temperature, and insolubles were filtered off. The filtrate was evaporated to dryness under reduced pressure to recover a solid. The solid was successively washed with water and toluene and then dried, to give 33.8 g (46.0% crude yield) of crude crystals of the desired product. The crude crystals were recrystallized using acetonitrile to give pale yellow purified crystals.

The melting point, thin layer chromatography Rf value, NMR and mass-spectral data of the obtained crystals were as follows.

mp. 162-164° C.

TLC (silica gel, chloroform/ethyl acetate=9/1): Rf=0.64

NMR (CD$_3$OD): δ6.8-8.0 (m)

MS m/z(%):

290 (66), 288 (M+, 100), 261 (3), 253 (3), 226 (3), 218 (3), 199 (3), 185 (5), 157 (3), 150 (7), 123 (17), 117 (13), 114 (13), 104 (5), 89 (15), 77 (10)

The obtained compound was identified, based on the spectral data, as 2-phenyl-4-(2,4-dichlorophenyl) imidazole, represented by the following structural formula (4).

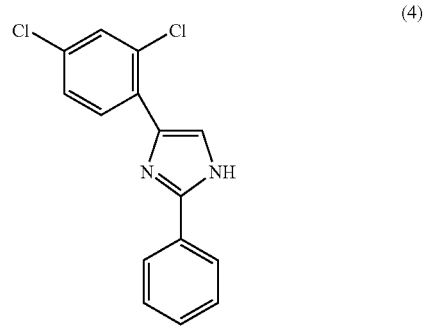

(4)

Example 1-2

Synthesis of 2-phenyl-4-(3,4-dichlorophenyl)imidazole 43.9 g (0.275 mol) of bromine was added dropwise to a solution of 50.5 g (0.267 mol) of 3',4'-dichloro acetophenone in 120 g of methanol at a reaction temperature of 50 to 55° C. After the addition was complete, the methanol was evaporated off the reaction solution under reduced pressure. The resultant concentrate was dissolved in 120 g of toluene and was then washed with water (150 ml×3 times). Thereafter, the toluene was evaporated off under reduced pressure, giving 68.0 g (0.254 mol) of crude brown oily 2-bromo-3',4'-dichloroacetophenone.

A solution of 68.0 g (0.254 mol) of the above-mentioned crude 2-bromo-3',4'-dichloroacetophenone in 110 ml of tetrahydrofuran was added dropwise over 30 minutes, under reflux with heating, into a suspension of 39.8 g (0.254 mol) of benzamidine hydrochloride, 102.1 g (1.02 mol) of potassium bicarbonate in 400 ml of tetrahydrofuran and 100 ml of water. After the addition was complete, further refluxing with heating was carried out for 2 hours. The reaction solution was evaporated to dryness under reduced pressure, to give a residual solid. This solid was successively washed with water and toluene, to give 45.5 g (62.0% crude yield) of crude crystals of the desired product. The crude crystals were recrystallized using acetonitrile, to give a purified white powder.

The melting point, thin layer chromatography Rf value, NMR and mass-spectral data of the obtained crystal were as follows.

mp. 179-182° C.

TLC (silica gel, chloroform/ethyl acetate=9/1): Rf=0.52

NMR (CD$_3$OD): δ 7.4-8.0 (m)

MS m/z(%):

290 (64), 288 (M+, 100), 253 (4), 226 (4), 185 (4), 150 (12), 123 (21), 117 (15), 104 (6), 89 (12), 77 (10)

The obtained compound was identified, based on the spectral data, as 2-phenyl-4-(3,4-dichlorophenyl) imidazole, represented by the following structural formula (5).

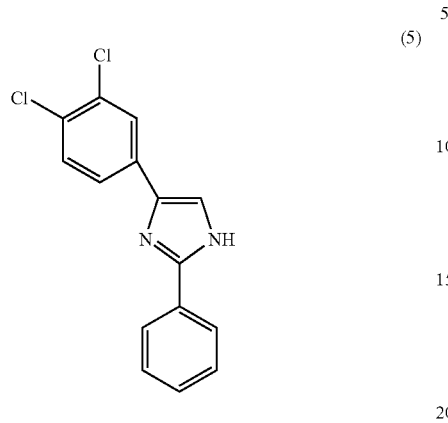

(5)

Example 1-3

Synthesis of
2-phenyl-4-(2,4-dichlorophenyl)-5-methylimidazole 51.4 g (0.322 mol) of bromine was added dropwise to a solution of 63.2 g (0.311 mol) of 2',4'-dichloropropiophenone in 140 g of methanol at a reaction temperature of 50 to 55° C. After the addition was complete, the methanol was evaporated off from the reaction solution under reduced pressure. The resultant concentrate was dissolved in 120 g of toluene and was then washed with water (150 ml×3 times). Thereafter, the toluene was distilled off under reduced pressure, giving 85.2 g (0.302 mol) of crude brown oily 2-bromo-2',4'-dichloropropiophenone.

A suspension of 47.3 g (0.302 mol) of benzamidine hydrochloride, 16.3 g (0.302 mol) of sodium methylate in 250 ml of tetrahydrofuran was heated under reflux for 1 hour, and cooled to 25° C. A solution of 85.2 g (0.302 mol) of the above-mentioned crude 2-bromo-2',4'-dichloropropiophenone in 160 ml of tetrahydrofuran was added dropwise in such a manner that the reaction temperature did not exceed 30° C. After the addition was complete, 16.3 g (0.302 mol) of sodium methylate was added, and the resultant was heated under reflux for 1 hour. Subsequently, the reaction solution was cooled to room temperature, and insolubles were then filtered off. The filtrate was evaporated to dryness under reduced pressure, to recover a residual solid. This solid was successively washed with water and toluene and then dried, to give 50.4 g (55.0% crude yield) of crude crystals of the desired product. The crude crystals were recrystallized using a mixture of acetonitrile and DMF, to give colorless purified crystals.

The melting point, thin layer chromatography Rf value, NMR and mass-spectral data of the obtained crystals were as follows.

mp. 222-224° C.

TLC (silica gel, acetone): Rf=0.67

NMR (d6-DMSO): δ2.19 (s, 3H), 7.2-8.1 (m, 8H)

MS m/z(%):

304 (65), 302 (M+, 100), 267 (14), 232 (4), 198 (3), 172 (4), 164 (11), 130 (8), 104 (17), 89 (15), 77 (13)

The obtained compound was identified, based on the spectral data, as 2-phenyl-4-(2,4-dichlorophenyl)-5-methylimidazole, represented by the following structural formula (6).

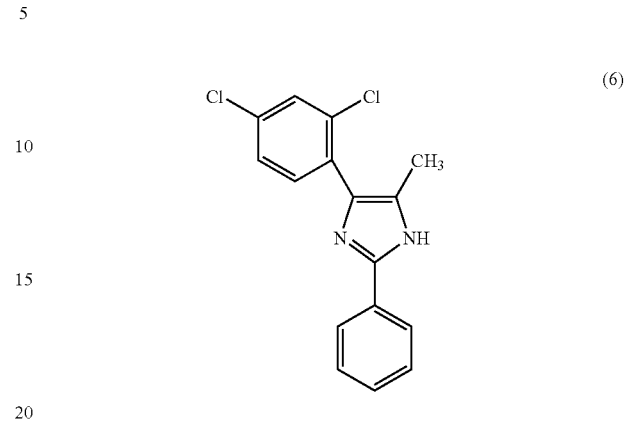

(6)

Example 1-4

Synthesis of
2-phenyl-4-(3,4-dichlorophenyl)-5-methylimidazole 51.1 g (0.320 mol) of bromine was added dropwise to a solution of 65.0 g (0.320 mol) of 3',4'-dichloropropiophenone in 150 g of methanol at a reaction temperature of 58 to 60° C. After the addition was complete, the methanol was evaporated off from the reaction solution under reduced pressure. The resultant concentrate was dissolved in 130 g of toluene and then washed with water (150 ml×3 times). Thereafter, the toluene was evaporated off under reduced pressure, giving 86.6 g (0.307 mol) of crude brown oily 2-bromo-3',4'-dichloropropiophenone.

A solution of 86.6 g (0.307 mol) of the above-mentioned crude 2-bromo-3',4'-dichloropropiophenone in 120 ml of tetrahydrofuran was added dropwise over 40 minutes into a suspension, under reflux with heating, of 48.1 g (0.307 mol) of benzamidine hydrochloride, 123.4 g (1.23 mol) of potassium bicarbonate in 450 ml of tetrahydrofuran and 110 ml of water. After the addition was complete, further refluxing with heating was carried out for 2 hours. The reaction solution was evaporated to dryness under reduced pressure, to give a residual solid. This solid was successively washed with water and toluene, to give 65.3 g (71.3% crude yield) of crude crystals of the desired product. The crude crystals were recrystallized using acetonitrile, to give a purified white powder.

The melting point, thin layer chromatography Rf value, NMR and mass-spectral data of the obtained crystals were as follows.

mp. 169-171° C.

TLC (silica gel, acetone): Rf=0.68

NMR (CD₃OD): δ 2.4 (s, 3H), 7.2-8.0 (m, 8H)

MS m/z(%):

304 (69), 302 (M+, 100), 266 (6), 231 (6), 198 (5), 164 (7), 130 (6), 104 (16), 89 (12), 77 (12)

The obtained compound was identified, based on the spectral data, as 2-phenyl-4-(3,4-dichlorophenyl)-5-methylimidazole, represented by the following structural formula (7).

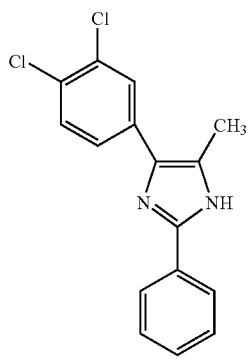

(7)

Next, Examples 2-1 to 2-5, in which a 2-(dichlorophenyl)-4-phenylimidazole compound is synthesized, are described. Starting materials used in each Example are obtained as described in the following.

Starting Material 2-acetoxyacetophenone (synthesized as described in Reference Examples described below)

1-phenyl-1,2-propanedione (manufactured by Tokyo Kasei Kogyo Co., Ltd., reagent)

2,3-dichlorobenzaldehyde (manufactured by Tokyo Kasei Kogyo Co., Ltd., reagent)

2,4-dichlorobenzaldehyde (manufactured by Tokyo Kasei Kogyo Co., Ltd., reagent)

2,6-dichlorobenzaldehyde (manufactured by Tokyo Kasei Kogyo Co., Ltd., reagent)

3,4-dichlorobenzaldehyde (manufactured by Tokyo Kasei Kogyo Co., Ltd., reagent)

Reference Example 1

Synthesis of 2-acetoxyacetophenone 78.5 g (0.80 mol) of potassium acetate, 5.0 g (0.08 mol) of acetic acid and 123.7 g (0.80 mol) of 2-chloroacetophenone was heated under reflux in 500 ml of ethanol for 6 hours. After the completion of heating, the reaction solution was cooled to room temperature, precipitated potassium chloride was filtered off, and ethanol was evaporated off under reduced pressure, giving an oily and caramel-like substance. The obtained oily substance was poured into 1 liter of water and the precipitated yellowish-brown crystalline solid was filtered off, followed by recrystallization from methanol, giving 113.1 g (0.635 mol, 79.3% yield) 2-acetoxyacetophenone.

Example 2-1

Synthesis of 2-(2,3-dichlorophenyl)-4-phenylimidazole

A solution of 43.9 g (0.22 mol) of copper (II) acetate.monohydrate dissolved in 150 ml of 25% ammonia water was added in small portions with water cooling to a solution of 17.8 g (0.1 mol) of 2-acetoxyacetophenone and 17.5 g (0.1 mol) of 2,3-dichlorobenzaldehyde dissolved in 120 ml of isopropyl alcohol. Subsequently, the temperature was raised to 60° C. over 1 hour and then raised to 78° C. over 3 hours.

After the completion of reaction, the reaction solution was cooled to 5° C., and the precipitate was filtered off and washed with water and then dried, giving 31.1 g of a deep-green powdery substance. The powdery substance was suspended in 160 ml of methanol and thereto was added 4.9 g (0.06 mol) of 70% sodium hydrosulfide, and the resultant was heated under reflux for 1 hour. Thereafter, the methanol solution was cooled and black insolubles were filtered off. Subsequently, the methanol was evaporated off under reduced pressure. The obtained residue was dissolved into chloroform and was then washed with water. Thereafter, chloroform was evaporated off under reduced pressure, and the resulting residue produced was recrystallized with acetonitrile, giving 12.5 g of gray powdery crystals (43% yield).

The melting point, thin layer chromatography Rf value, NMR and mass-spectral data of the obtained crystals were as follows.

mp. 144-146° C.

TLC (silica gel, chloroform/ethyl acetate=9/1): Rf=0.51

NMR (CDCl$_3$): δ 7.2-8.4 (m)

MS m/z(%): 290 (70), 288 (M+, 100), 253 (7), 123 (4), 117 (9), 89 (19)

The obtained crystals were identified, based on the spectral data, as 2-(2,3-dichlorophenyl)-4-phenylimidazole, represented by the following structural formula (8).

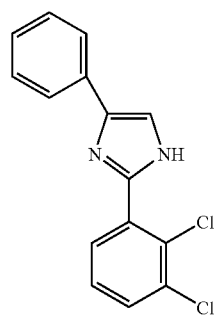

(8)

Example 2-2

Synthesis of 2-(2,4-dichlorophenyl)-4-phenylimidazole

A solution of 43.9 g (0.22 mol) of copper (II) acetate.hydrate was dissolved in 160 ml of 25% ammonia water was added in small portions with water cooling to a solution of 17.8 g (0.1 mol) of 2-acetoxyacetophenone and 17.5 g (0.1 mol) of 2,4-dichlorobenzaldehyde dissolved in 150 ml of isopropyl alcohol. Subsequently, the temperature was raised to 60° C. over 1 hour and then raised to 80° C. over 2.5 hours.

After the completion of reaction, the reaction solution was cooled to 10° C., and the precipitate was filtered off and washed with water and then dried, giving 27.3 g of a deep-green powdery substance. The powdery substance was suspended in 150 ml of methanol and thereto was added 4.3 g (0.054 mol) of 70% sodium hydrosulfide, and the resultant was heated under reflux for 1 hour. Thereafter, the methanol solution was cooled and black insolubles were filtered off. Subsequently, the methanol was evaporated off from the reaction solution under reduced pressure. The obtained residue was dissolved in chloroform and then washed with water.

Thereafter, chloroform was evaporated off under reduced pressure, and the resulting residue produced was recrystallized with acetonitrile, giving 11.0 g of yellow powdery crystals (38% yield).

The melting point, thin layer chromatography Rf value, NMR and mass-spectral data of the obtained crystals were as follows.

mp. 153-156° C.

TLC (silica gel, chloroform/ethyl acetate=9/1): Rf=0.56

NMR (CDCl$_3$): δ 7.0-8.5 (m)

MS m/z(%): 290 (66), 288 (M+, 100), 253 (5), 226 (4), 185 (5), 171 (4), 144 (4), 123 (7), 117 (15), 100 (4), 89 (19)

The obtained crystals were identified, based on the spectral data, as 2-(2,4-dichlorophenyl)-4-phenylimidazole, represented by the following structural formula (9).

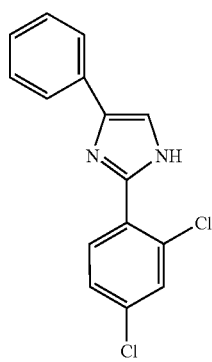

(9)

Example 2-3

Synthesis of 2-(2,3-dichlorophenyl)-4-phenyl-5-methylimidazole 14.8 g (0.1 mol) of 1-phenyl-1,2-propandione, 17.5 g (0.1 mol) of 2,3-dichlorobenzaldehyde and 46.2 g (0.6 mol) of ammonium acetate were heated under reflux in 100 ml of acetic acid for 5 hours. After the completion of reaction, the reaction solution was allowed to cool to room temperature, and poured into a large amount of dilute ammonia water. The precipitated solid was filtered off and washed with water, followed by recrystallization from acetonitrile, giving 17.3 g of light-green powdery crystals (57% yield).

The melting point, thin layer chromatography Rf value, NMR, and mass-spectral data of the obtained crystals were as follows.

mp. 183-185° C.

TLC (silica gel, chloroform/ethyl acetate=9/1): Rf=0.60

NMR (CDCl$_3$): δ2.5 (s, 3H), 7.2-8.3 (m, 8H)

MS m/z(%): 304 (69), 302 (M+, 100), 267 (3), 225 (2), 172 (6), 151 (5), 130 (35), 103 (30), 89 (20), 77 (19)

The obtained crystals were identified, based on the spectral data, as 2-(2,3-dichlorophenyl)-4-phenyl-5-methylimidazole, represented by the following structural formula (10).

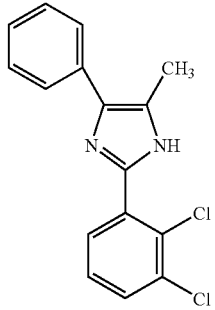

(10)

Example 2-4

Synthesis of 2-(2,6-dichlorophenyl)-4-phenyl-5-methylimidazole 14.8 g (0.1 mol) of 1-phenyl-1,2-propandione, 17.5 g (0.1 mol) of 2,6-dichlorobenzaldehyde and 46.2 g (0.6 mol) of ammonium acetate were heated under reflux in 100 ml of acetic acid for 5 hours. After the completion of reaction, the obtained reaction solution was allowed to cool to room temperature, and was poured into a large amount of dilute ammonia water. The precipitated solid was filtered off and washed with water and then dried, giving 30.4 g of a brown solid. The obtained solid was dissolved in 150 ml of chloroform, and concentrated hydrochloric acid was added thereto to precipitate hydrochloride. The precipitated hydrochloride was filtered off and washed with acetone and then dissolved in methanol. Sodium methylate-methanol solution was added thereto for dehydrochlorination. Subsequently, the methanol was evaporated off from the resulting solution under reduced pressure and the obtained solid was washed with water and then dried, giving 18.5 g of opalescent powdery crystals (61% yield).

The melting point, thin layer chromatography Rf value, NMR and mass-spectral data of the obtained crystals were as follows.

mp. 185-189° C.

TLC (silica gel, chloroform/ethyl acetate=9/1): Rf=0.49

NMR (CDCl$_3$): δ2.5 (s, 3H), 7.2-7.7 (m, 8H)

MS m/z(%): 304 (66), 302 (M+, 100), 267 (2), 225 (2), 199 (2), 172 (6), 151 (4), 130 (39), 103 (29), 89 (31), 77 (19)

The obtained crystals were identified, based on the spectral data, as 2-(2,6-dichlorophenyl)-4-phenyl-5-methylimidazole, represented by the following structural formula (11).

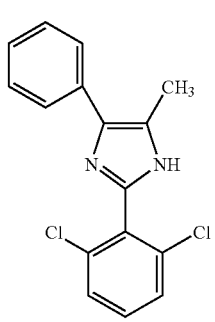

(11)

Example 2-5

Synthesis of 2-(3,4-dichlorophenyl)-4-pheny-5-methylimidazole 14.8 g (0.1 mol) of 1-phenyl-1,2-propandione, 17.5 g (0.1 mol) of 3,4-dichlorobenzaldehyde and 46.2 g (0.6 mol) of ammonium acetate were heated under reflux in 100 ml of acetic acid for 5 hours. After the completion of reaction, the obtained reaction solution was allowed to cool to room temperature, and poured into a large amount of dilute ammonia water. The precipitated solid was filtered off and washed with water, followed by recrystallization from methanol, giving 18.8 g of powdery pale yellow crystals (62% yield).

The melting point, thin layer chromatography Rf value, NMR, and mass-spectral data of the obtained crystals were as follows.

mp. 172-175° C.
TLC (silica gel, chloroform/ethyl acetate=9/1): Rf=0.60
NMR (CDCl$_3$): δ2.5 (s, 3H), 7.3-7.9 (m, 8H)
MS m/z(%): 304 (63), 302 (M+, 100), 267 (3), 225 (3), 199 (2), 172 (7), 151 (4), 130 (25), 103 (20), 89 (12), 77 (15)

The obtained crystal was identified, based on the spectral data, as 2-(3,4-dichlorophenyl)-4-phenyl-5-methylimidazole represented by the following structural formula (12).

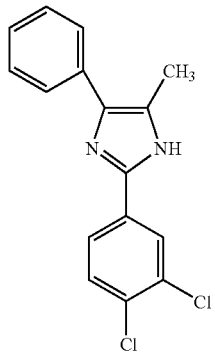

(12)

Next, a surface treatment agent and surface treatment composition containing the imidazole compound of the invention are described. The processes used for synthesizing the imidazole compounds are as follows.

Imidazole Compounds 2-(2,3-dichlorophenyl)-4-phenylimidazole was synthesized according to Example 2-1.

2-(2,4-dichlorophenyl)-4-phenylimidazole was synthesized according to Example 2-2.

2-(2,3-dichlorophenyl)-4-phenyl-5-methylimidazole was synthesized according to Example 2-3.

2-(2,6-dichlorophenyl)-4-phenyl-5-methylimidazole was synthesized according to Example 2-4.

2-(3,4-dichlorophenyl)-4-phenyl-5-methylimidazole was synthesized according to Example 2-5.

2-phenyl-4-(2,4-dichlorophenyl)imidazole was synthesized according to Example 1-1.

2-phenyl-4-(3,4-dichlorophenyl)imidazole was synthesized according to Example 1-2.

2-phenyl-4-(2,4-dichlorophenyl)-5-methylimidazole was synthesized according to Example 1-3.

2-phenyl-4-(3,4-dichlorophenyl)-5-methylimidazole was synthesized according to Example 1-4.

Synthesis of 2-(2,4-dichlorophenyl)-4-phenyl-5-methylimidazole 14.8 g (0.1 mol) of 1-phenyl-1,2-propandione, 17.5 g (0.1 mol) of 2,4-dichlorobenzaldehyde and 46.2 g (0.6 mol) of ammonium acetate were heated under reflux in 100 ml of acetic acid for 5 hours. After the completion of reaction, the obtained reaction solution was allowed to cool to a room temperature, and poured into a large amount of dilute ammonia water. The precipitated solid was filtered off and washed with water, followed by recrystallization from methanol, giving 16.4 g of colorless powdery crystals (54% yield).

The melting point, thin layer chromatography Rf value, NMR, and mass-spectral data of the obtained crystals were as follows.

mp. 143-145° C.
TLC (silica gel, chloroform/ethyl acetate=9/1): Rf=0.65
NMR (CDCl$_3$): δ2.5 (s, 3H), 7.3-8.4 (m, 8H)
MS m/z(%): 304 (69), 302 (M+, 100), 267 (2), 225 (2), 199 (2), 172 (6), 151 (4), 130 (31), 103 (23), 89 (17), 77 (17)

2,4-diphenylimidazole and 2,4-diphenyl-5-methylimidazole were synthesized by the method disclosed in Japanese Unexamined Patent Publication No. 7-243053.

2-(4-chlorophenyl)-4-phenylimidazole was synthesized in accordance with the synthesis method disclosed in Examples 2-1 and 2-2 of this specification. 4-chlorobenzaldehyde was used as the benzaldehyde compound to be used as a starting material.

2-(4-chlorophenyl)-4-phenyl-5-methylimidazole was synthesized according to the synthesis method disclosed in Examples 2-3 and 2-4 of this specification. 4-chlorobenzaldehyde was used as the benzaldehyde compound to be used as a starting material.

2-phenyl-4-(4-chlorophenyl)imidazole was synthesized in accordance with the synthesis method disclosed in Examples 1-1 and 1-2 of this specification. 4'-chloroacetophenone was used as the acetophenone compound to be used as a starting material.

2-phenyl-4-(4-chlorophenyl)-5-methylimidazole was synthesized in accordance with the synthesis method disclosed in Examples 1-3 and 1-4 of this specification. 4'-chloropropiophenone was used as the propiophenone compound to be used as a starting material.

The evaluation test method for the surface treatment compositions prepared in Examples 3-1 to 3-10 and Comparative Examples 3-1 to 3-6, which are described later, is explained below.

Evaluation Test for Solder Flow-Up Rate Properties

Printed wiring boards made of a glass epoxy resin measuring 120 mm (length)×150 mm (width)×1.6 mm (thickness) having 300 copper through-holes with an inner diameter of 0.80 mm was used as test pieces. Each test piece was degreased with an acid-based cleaner, and soft-etched using a sulfuric acid/hydrogen peroxide-based chemical agent and was then rinsed with water. Thereafter, the test piece was immersed in the surface treatment composition kept at a liquid temperature as shown in Table 1 for a predetermined time as shown in Table 1, followed by washing with water and drying, to form a chemical layer about 0.1 to about 0.5 μm thickness on the copper surface.

The surface-treated test piece was subjected to three cycles of reflow-heating in which the peak temperature was 240° C. using an infrared reflow oven (trade name: MULTI-PRO-306, manufactured by Vetronix Co., Ltd.) and subsequently soldering was performed with a flow soldering device (conveyor speed: 1.0 m/minute).

The solder used was a tin-lead eutectic solder with a composition of 63% tin and 37% lead (% by weight) (trade name: H63A, manufactured by Senju Metal Industry Co., Ltd.), and the flux used for soldering was JS-64MSS (manufactured by KOKI Co., Ltd.). The soldering temperature was 240° C.

Test piece surface treated as above were also soldered using lead-free solder in the same manner as for the tin-lead eutectic solder. The solder used was lead-free solder (trade name: H705 "ECOSOLDER", manufactured by Senju Metal Industry Co., Ltd.) with a composition of 96.5% tin, 3.0% silver and 0.5% copper (% by weight), and the flux used for soldering was JS-E-09 (manufactured by KOKI Co., Ltd.). The reflow-heating peak temperature was 245° C., and the soldering temperature was also 245° C.

For the soldered test piece, the measured result was indicated by the proportion (%) of the number of copper through-holes in which the solder was filled up to the copper land of the copper through-holes with respect to the total number of copper through-holes (300 holes).

When the solder wettability on the copper surface is large, the molten solder penetrates inside each copper through-hole, whereby the molten solder readily fills it to the upper land of the through-hole. More specifically, if the number of through-holes whose upper lands were soldered was large, solder wettability and solderability to the copper would be judged to be excellent.

Evaluation Test for Solder Spreadability

Printed wiring boards made of a glass epoxy resin measuring 50 mm (length)×50 mm (width)×1.2 mm (thickness) was used as test pieces. Each printed wiring board had a circuit pattern in which 10 pieces of a copper-foiled circuit with a conductor width of 0.80 mm and a length of 20 mm were formed in a width direction at intervals of 1.0 mm. The test piece was degreased with an acid-based cleaner, soft-etched using a sulfuric acid/hydrogen peroxide based chemical agent, and was then washed with water. Thereafter, the test piece was immersed in a surface treatment agent kept at a liquid temperature as shown in Table 1 for a predetermined time as shown in Table 1, followed by washing with water and drying, to form a chemical layer about 0.10 to 0.50 μm thickness on the copper surface.

The surface-treated test piece was subjected to one cycle of reflow-heating in which the peak temperature was 240° C. using an infrared reflow oven (trade name: MULTI-PRO-306, manufactured by Vetronix Co., Ltd.). Thereafter, a tin-lead solder paste was printed on the center of the copper circuits using a metal mask of 1.2 mm aperture diameter and 150 μm thickness, and reflow-heating was conducted at the above-described conditions for soldering. The tin-lead solder paste used was an eutectic solder (trade name: OZ-63-330F-40-10, manufactured by Senju Metal Industry Co., Ltd.) composed of 63% tin and 37% lead (% by weight).

Test pieces surface treated as above were also soldered using lead-free solder paste in the same manner for the tin-lead solder paste. The lead-free solder used was composed of 96.5% tin, 3.0% silver and 0.5% copper (% by weight) (trade name: M705-221BM5-42-11, manufactured by Senju Metal Industry Co., Ltd.). The peak temperature of reflow-heating attained before and after the solder paste printing was set to 245° C.

The length (mm) of solder which wet and spread over the copper circuit of the obtained test piece was measured.

When the length was longer, solder wettability and solderability would be judged to be excellent.

Example 3-1

2-(2,3-dichlorophenyl)-4-phenyl-5-methylimidazole as an imidazole compound, acetic acid as an acid, copper acetate as a metal salt and ammonium bromide as a halide were dissolved in ion-exchanged water so that a composition as shown in Table 1 was obtained. The pH was then adjusted to 3.1 with ammonia water to prepare a surface treatment composition.

Subsequently, a printed wiring board test piece was immersed for 60 seconds in the surface treatment agent whose temperature had been adjusted to 40° C., followed by washing with water and drying. The solder flow-up rate and spreadability of the solder paste were then measured.

Examples 3-2 to 3-10, Comparative Examples 1 to 6

Compositions for surface treatment having the compositions shown in Table 1 were prepared in the same manner as in Example 3-1. Subsequently, surface treatment was conducted at the conditions shown in Table 1, followed by washing with water and drying. The solder flow-up rate and spreadability of the solder paste were then measured.

Table 1 shows the test results of each composition prepared in Examples 3-1 to 3-10 and Comparative examples 1 to 6.

TABLE 1

| | | | Examples | | | | | | | |
|---|---|---|---|---|---|---|---|---|---|---|
| | | | 3-1 | 3-2 | 3-3 | 3-4 | 3-5 | 3-6 | 3-7 | 3-8 |
| Surface Treatment Composition (% by weight) | Imidazole Compound | 2-(2,3-dichlorophenyl)-4-phenyl-5-methylimidazole | 0.25 | | | | | | | |
| | | 2-(2,4-dichlorophenyl)-4-phenyl-5-methylimidazole | | 0.5 | | | | | | |
| | | 2-(2,6-dichlorophenyl)-4-phenyl-5-methylimidazole | | | 0.25 | | | | | |
| | | 2-(3,4-dichlorophenyl)-4-phenyl-5-methylimidazole | | | | 0.25 | | | | |
| | | 2-phenyl-4-(2,4-dichlorophenyl)-5-methylimidazole | | | | | | 0.25 | | |
| | | 2-phenyl-4-(3,4-dichlorophenyl)-5-methylimidazole | | | | | | | 0.25 | |

TABLE 1-continued

| Category | Component | | | | | | | | |
|---|---|---|---|---|---|---|---|---|---|
| | 2-(2,3-dichlorophenyl)-4-phenylimidazole | | | | | | | 0.15 | |
| | 2-(2,4-dichlorophenyl)-4-phenylimidazole | | | | | | | | 0.1 |
| | 2-phenyl-4-(2,4-dichlorophenyl)imidazole | | | | | | | | |
| | 2-phenyl-4-(3,4-dichlorophenyl)imidazole | | | | | | | | |
| | 2,4-diphenyl-5-mehylimidazole | | | | | | | | |
| | 2-(4-chlorophenyl)-4-phenyl-5-methylimidazole | | | | | | | | |
| | 2-phenyl-4-(4-chlorophenyl)-5-methylimidazole | | | | | | | | |
| | 2,4-diphenylimidazole | | | | | | | | |
| | 2-(4-chlorophenyl)-4-phenylimidazole | | | | | | | | |
| | 2-phenyl-4-(4-chlorophenyl)imidazole | | | | | | | | |
| Acid | formic acid | | | | | | 10 | | |
| | acetic acid | 12 | 20 | 10 | 25 | | | 32 | 25 |
| | lactic acid | | | | | 10 | | | |
| | n-heptanoic acid | | 0.10 | | 0.20 | | | | |
| Metal Salt | copper acetate | 0.10 | | 0.10 | 0.10 | | | | |
| | copper (I) chloride | | | | | | | 0.05 | |
| | copper (I) bromide | | | | | | | | 0.07 |
| | copper (II) bromide | | | | | 0.10 | | | |
| | copper iodide | | | | | | 0.09 | | |
| | zinc acetate | | | | | | | | |
| | zinc chloride | | | | 0.60 | | | | |
| Halogen | ammonium chloride | | | | 0.15 | | | | |
| | potassium chloride | | | | | | | | |
| | ammonium bromide | 0.06 | | | | | | | |
| | potassium bromide | | | | | | | | |
| | ammonium iodide | | | 0.03 | | | | | |
| | potassium iodide | | | | | | | | |
| | pH | 3.1 | 2.5 | 3.5 | 2.7 | 3.2 | 1.9 | 3.8 | 3.3 |
| Treatment Condition | Treatment temperature (° C.) | 40 | 30 | 50 | 60 | 40 | 40 | 50 | 50 |
| | Treatment time (seconds) | 60 | 120 | 60 | 60 | 120 | 180 | 60 | 120 |
| Evaluation Test | Solder flow-up rate property (%) Tin-lead eutectic solder (240° C.) | 91 | 99 | 100 | 100 | 92 | 98 | 94 | 99 |
| | Lead-free solder (245° C.) | 95 | 100 | 90 | 91 | 100 | 100 | 91 | 97 |
| | Solder spreadability (mm) Tin-lead eutectic solder (240° C.) | 2.89 | 3.72 | 3.18 | 3.29 | 3.58 | 3.97 | 3.68 | 3.28 |
| | Lead-free solder (245° C.) | 1.64 | 1.65 | 1.66 | 1.71 | 1.67 | 1.66 | 1.66 | 1.62 |

| | | Examples | | Comparative Examples | | | | | |
|---|---|---|---|---|---|---|---|---|---|
| | | 3-9 | 3-10 | 1 | 2 | 3 | 4 | 5 | 6 |
| Surface Treatment Composition (% by weight) | Imidazole Compound | | | | | | | | |
| | 2-(2,3-dichlorophenyl)-4-phenyl-5-methylimidazole | | | | | | | | |
| | 2-(2,4-dichlorophenyl)-4-phenyl-5-methylimidazole | | | | | | | | |
| | 2-(2,6-dichlorophenyl)-4-phenyl-5-methylimidazole | | | | | | | | |
| | 2-(3,4-dichlorophenyl)-4-phenyl-5-methylimidazole | | | | | | | | |
| | 2-phenyl-4-(2,4-dichlorophenyl)-5-methylimidazole | | | | | | | | |
| | 2-phenyl-4-(3,4-dichlorophenyl)-5-methylimidazole | | | | | | | | |
| | 2-(2,3-dichlorophenyl)-4-phenylimidazole | | | | | | | | |
| | 2-(2,4-dichlorophenyl)-4-phenylimidazole | | | | | | | | |
| | 2-phenyl-4-(2,4-dichlorophenyl)imidazole | 0.25 | | | | | | | |
| | 2-phenyl-4-(3,4-dichlorophenyl)imidazole | | 0.25 | | | | | | |
| | 2,4-diphenyl-5-mehylimidazole | | | 0.25 | | | | | |
| | 2-(4-chlorophenyl)-4-phenyl-5-methylimidazole | | | | 0.2 | | | | |

TABLE 1-continued

| | | | C1 | C2 | C3 | C4 | C5 | C6 | C7 | C8 |
|---|---|---|---|---|---|---|---|---|---|---|
| | | 2-phenyl-4-(4-chlorophenyl)-5-methylimidazole | | | | | 0.25 | | | |
| | | 2,4-diphenylimidazole | | | | | | 0.25 | | |
| | | 2-(4-chlorophenyl)-4-phenylimidazole | | | | | | | 0.25 | |
| | | 2-phenyl-4-(4-chlorophenyl)imidazole | | | | | | | | 0.25 |
| | Acid | formic acid | | | | | | | | |
| | | acetic acid | 20 | 30 | 10 | 10 | 10 | 10 | | 30 |
| | | lactic acid | | | | | | | 10 | |
| | | n-heptanoic acid | | | | | | | | 0.20 |
| | Metal Salt | copper acetate | 0.10 | 0.10 | 0.05 | 0.05 | 0.05 | 0.10 | 0.10 | 0.10 |
| | | copper (I) chloride | | | | | | | | |
| | | copper (I) bromide | | | | | | | | |
| | | copper (II) bromide | | | | | | | | |
| | | copper iodide | | | | | | | | |
| | | zinc acetate | | 1.0 | | 1.0 | | | | 2.0 |
| | | zinc chloride | | | | | | | | |
| | Halogen | ammonium chloride | | | 0.08 | | | | | |
| | | potassium chloride | | | | | | 0.10 | | |
| | | ammonium bromide | | | | 0.06 | | | | |
| | | potassium bromide | 0.06 | | | | | | 0.08 | |
| | | ammonium iodide | | | | | 0.05 | | | 0.06 |
| | | potassium iodide | | 0.08 | | | | | | |
| | | pH | 2.6 | 2.6 | 3.8 | 3.9 | 3.6 | 3.9 | 2.8 | 4.0 |
| | Treatment Condition | Treatment temperature (° C.) | 60 | 50 | 40 | 50 | 40 | 40 | 30 | 60 |
| | | Treatment time (seconds) | 180 | 180 | 60 | 60 | 120 | 90 | 180 | 180 |
| Evaluation Test | Solder flow-up rate property (%) | Tin-lead eutectic solder (240° C.) | 100 | 100 | 91 | 99 | 100 | 100 | 92 | 98 |
| | | Lead-free solder (245° C.) | 100 | 100 | 32 | 37 | 58 | 54 | 48 | 62 |
| | Solder spreadability (mm) | Tin-lead eutectic solder (240° C.) | 3.23 | 3.82 | 2.89 | 3.01 | 3.68 | 3.13 | 3.26 | 3.47 |
| | | Lead-free solder (245° C.) | 1.63 | 1.71 | 1.52 | 1.50 | 1.62 | 1.57 | 1.55 | 1.58 |

The test results shown in Table 1 are described hereafter. The imidazole compounds used in the present invention have, as shown in Examples 3-1 to 3-10, a basic 2,4-diphenylimidazole compound skeleton with two hydrogen atoms of one of the phenyl groups bonded to the 2- or 4-position of the imidazole skeleton being substituted with two chlorine atoms. In the imidazole compounds used in the Comparative Examples, the above-mentioned phenyl group is not substituted with chlorine atoms, or is substituted with only one chlorine atom.

As is evident from Table 1, the test results of Examples and Comparative Examples showed a 90 to 100% solder flow-up rate when soldering was conducted using a tin-lead eutectic solder, and few differences between Examples and Comparative Examples can be seen.

However, while the solder flow-up rate showed 90 to 100% in the case of using lead-free solder in Examples, it showed only about 30 to about 60% in the Comparative Examples. As evidenced above, it can be seen that when soldering was conducted using lead-free solder, the solder wettability was remarkably improved by treating the copper surface using the surface treatment composition of the present invention.

The value exhibiting solder spreadability when using a tin-lead eutectic solder was about 2.9 to about 4.0 mm in Examples and about 2.9 to about 3.7 mm in Comparative Examples, and thus it can be seen that the solder spreadability obtained in Examples was better than that in Comparative Examples. In contrast, when lead-free solder was used, the value exhibiting solder spreadability was about 1.6 to about 1.7 mm in Examples but about 1.5 to about 1.6 mm in Comparative Examples. As evidenced above, it can be seen that when soldering was conducted using lead-free solder, the solder wettability was remarkably improved by treating the copper surface using the surface treatment composition of the present invention.

These effects originate from the fact that the imidazole compounds of the present invention have a 2,4-diphenylimidazole compound skeleton in which two hydrogen atoms of one of the phenyl groups bonded to the 2- or 4-position of the imidazole skeleton is substituted with two chlorine atoms.

INDUSTRIAL APPLICABILITY

The imidazole compound of the invention can be suitably used as a component of a water-based surface treatment composition for copper or copper alloy at the time of soldering electronic components to copper or copper alloy circuit on a printed wiring board using lead-free solder.

The invention claimed is:

1. A soldering process comprising:
   contacting a copper or copper alloy-containing material with a water-based composition,
   the water-based composition comprising an imidazole compound, the imidazole compound is at least one member selected from the group consisting of 2-(2,3-dichlorophenyl)-4-phenyl-5-methylimidazole, 2-(2,6-dichlorophenyl)-4-phenyl-5-methylimidazole, 2-(3,4-dichlorophenyl)-4-phenyl-5-methylimidazole, 2-phenyl-4-(2,4-dichlorophenyl)-5-methylimidazole, 2-phenyl-4-(3,4-dichlorophenyl)-5-methylimidazole, 2-(2,3-dichlorophenyl)-4-phenylimidazole and 2-phenyl-4-(3,4-dichlorophenyl) imidazole, wherein the imidazole compound is present in an amount of 0.01 to 10% by weight based on the whole water-based composition and the water-based composition further comprising a copper compound, wherein the copper compound is at least one member selected from the group consisting of copper halides, copper salts of acids and copper hydroxide, and is present in an amount of 0.01 to 10% by weight based of the whole water-based composition, the water-based compound further comprising an acid, wherein the acid is present in an amount of 0.1 to 50% by weight based on the whole water-based composition, wherein the acid is at least one member selected from the group consisting of $C_1$-$C_{12}$ saturated aliphatic monocarboxylic acids, $C_1$-$C_{12}$ unsaturated aliphatic monocarboxylic acids, $C_2$-$C_6$ saturated aliphatic di-carboxylic acids, $C_2$-$C_6$ unsaturated aliphatic di-carboxylic acids, $C_7$ or $C_8$ aromatic carboxylic acids, $C_6$-$C_8$ aromatic sulfonic acids, hydrochloric acid, phosphoric acid, sulfuric acid and nitric acid, and soldering the copper or copper alloy-containing material using a lead-free solder.

* * * * *